United States Patent
Smith

[11] Patent Number: 6,106,149
[45] Date of Patent: Aug. 22, 2000

[54] MASS AND HEAT FLOW MEASUREMENT SENSOR

[75] Inventor: Allan L. Smith, 328 Pembroke Rd, Bala Cynwyd, Pa. 19004

[73] Assignee: Allan L. Smith, Bala Cynwyd, Pa.

[21] Appl. No.: 09/203,940

[22] Filed: Dec. 2, 1998

Related U.S. Application Data

[60] Provisional application No. 60/067,239, Dec. 2, 1997.

[51] Int. Cl.$^7$ ............................ G01K 17/00; G01K 13/00
[52] U.S. Cl. .............................. 374/31; 374/142; 374/43; 73/204.26
[58] Field of Search .............................. 374/142, 43, 45, 374/31, 32, 35; 73/204.12, 204.26, 580, 862.59, 24.01

[56] References Cited

U.S. PATENT DOCUMENTS

| | | | |
|---|---|---|---|
| 3,187,569 | 6/1965 | Los ....................................... | 73/204.12 |
| 4,492,480 | 1/1985 | Wadso et al. . | |
| 4,561,286 | 12/1985 | Sekler et al. . | |
| 4,596,697 | 6/1986 | Ballato . | |

(List continued on next page.)

OTHER PUBLICATIONS

In Situ Interfacial Mass Detection with Piezoelectric Transducers, M.D. and Buttry, D.A., Science, vol. 249, pp. 1000–1007, (1990).

Cell Proliferation in Carcinogenis, Cohen, S.M., and Ellwein, L.B.,Analytical Chemistry, vol. 65, pp. 940A–948A, 987A–996A, (1993).

The Problem of Counting the Number of Molecules and Calculating Thermodynamic Properties, Torres, L.A., Hernandez and Guardado, J.A., Journal of Chemical Education, vol. 72, pp. 67–70, (1995).

Piezoelectric Crystals for Mass and Chemical Measurements, Alder, J.F. and McCallum, J.J., Analyst, vol. 108, pp. 1169–1189, (1983).

Piezoelectric Devices for Mass and Chemical Measurements: an Update, John J. McCallum, Analyst, vol. 114, pp. 1173–1189, (1989).

Trends in Isothermal Microcalorimetry, Wadso, I., Chemical Society Reviews, pp. 79–86, (1997).

Heat Conduction Calorimeters: time constants, sensitivity, and fast titration experiments, Backman, P., Bastos, M. Hallen, D., Lonnbro, P. and Wadso, I., Journal of Biochemical and Biophysical Methods, vol. 28, pp. 85–100, (1994).

Standard reference material proposed for enthalpy–of–sublimation measurements. A comparitive study of the standard molar enthalpy of sublimation of Fe (ferrocene) by calorimetry and Knudsen–effusion techniques, Torres, L.A., Gudino, R. No Date.

(List continued on next page.)

*Primary Examiner*—Diego Gutierrez
*Assistant Examiner*—Yaritza Guadalupe
*Attorney, Agent, or Firm*—Sampson & Associates, P.C.

[57] ABSTRACT

Provided are mass and heat flow measurement sensors comprising a microresonator, such as a quartz crystal microbalance; a heat flow sensor, such as an isothermal heat conduction calorimeter; and a heat sink coupled thermally to the heat flow sensor. The microresonator may be used to measure changes of mass due to a sample at its surface, and heat flow sensor, which is coupled thermally to the microresonator, may be used to measure heat flow from the sample on the surface of the microresonator to the heat sink. Also provided are methods for measuring the mass of a sample and the flow of heat from the sample to the heat sink by utilizing such mass and heat flow measurement sensors.

67 Claims, 3 Drawing Sheets

U.S. PATENT DOCUMENTS

| | | |
|---|---|---|
| 4,741,200 | 5/1988 | Hammerle . |
| 4,788,466 | 11/1988 | Paul et al. . |
| 4,821,303 | 4/1989 | Fawcett et al. . |
| 4,872,765 | 10/1989 | Schodowski . |
| 5,036,701 | 8/1991 | van der Graaf ............ 73/204.12 |
| 5,151,110 | 9/1992 | Bein et al. . |
| 5,201,215 | 4/1993 | Granstaff et al. . |
| 5,207,765 | 5/1993 | Eiermann et al. ............ 73/204.26 |
| 5,220,836 | 6/1993 | Harns et al. ............ 73/862.59 |
| 5,265,479 | 11/1993 | Cook et al. ............ 73/862.59 |
| 5,295,745 | 3/1994 | Cassettari et al. . |
| 5,306,644 | 4/1994 | Myerholtz et al. . |
| 5,312,587 | 5/1994 | Templer et al. . |
| 5,339,051 | 8/1994 | Koehler et al. . |
| 5,347,861 | 9/1994 | Satoh ............ 73/204.12 |
| 5,452,610 | 9/1995 | Kleinhans ............ 73/204.26 |
| 5,476,002 | 12/1995 | Bowers et al. . |
| 5,686,779 | 11/1997 | Vig . |
| 5,705,399 | 1/1998 | Larue . |
| 5,705,745 | 1/1998 | Treutler et al. ............ 73/204.12 |
| 5,719,324 | 2/1998 | Thundat et al. . |
| 5,734,098 | 3/1998 | Kraus et al. . |
| 5,739,416 | 4/1998 | Hoenk . |
| 5,744,902 | 4/1998 | Vig . |
| 5,763,775 | 6/1998 | Sato et al. ............ 73/204.26 |
| 5,768,937 | 6/1998 | Wajid et al. ............ 73/24.01 |
| 5,779,362 | 7/1998 | Lightfoot . |
| 5,795,993 | 8/1998 | Pfeifer et al. . |
| 5,798,452 | 8/1998 | Martin et al. . |
| 5,817,933 | 10/1998 | Daetz ............ 73/204.26 |
| 5,852,239 | 12/1998 | Sato et al. ............ 73/204.26 |
| 5,910,647 | 1/1999 | Kats et al. ............ 73/580 |
| 5,869,763 | 2/1999 | Vig et al. ............ 73/580 |
| 6,029,500 | 2/2000 | Tom ............ 73/24.01 |

OTHER PUBLICATIONS

Using the quartz crystal microbalance principle for gas detection with reversible and irreversible sensors, Hartmann, J., Auge, J. and Hauptmann, P., Sensors and Actuators B, 18–19, pp. 429–433, (1994).

Gravimetric, dielectric and calorimetric methods for the detection of organic solvent vapours using poly (ether urethane) coatings, Zhou, R., Hierlemann, A., Weimar, U. and Gopel, W., Sensors and Actuators B 34, pp. 356–360, (1996).

FIG. 1
PRIOR ART
$$\begin{cases} Q = C\Delta T \\ Q = \int (dQ/dt)\, dt \end{cases}$$

$$P = \frac{1}{S}\left[ U + \tau\left(\frac{dU}{dt}\right) \right]$$

MASS AND HEAT FLOW MEASUREMENT SENSOR

RELATED APPLICATION

This application claims priority to U.S. Provisional Patent Application No. 60/067,239, filed Dec. 2, 1997.

FIELD OF THE INVENTION

The present invention pertains generally to the field of sensors for the measurement of changes in mass and heat flow. More particularly, the present invention pertains to a combined microresonator mass sensor and heat flow sensor which may provide simultaneous and continuous measurement of the changes in mass and heat flow at a gas-solid interface.

BACKGROUND OF THE INVENTION

Although the piezoelectric effect has been known since the 19th century, the development of quartz crystal devices which oscillate at precisely defined resonant frequencies and which can be incorporated as passive elements into electronic instruments began in the 1920's. Like much of our modern electronic technology, their development received a massive push during World War II, when over 30 million quartz crystal oscillators were produced for use in military communications equipment. Today there is widespread use of quartz crystal oscillators and of newer types of microresonators in electronics wherever precise control of frequency is needed as, for example, in radio frequency communications, in frequency meters and timepieces, in scientific instrumentation, and in computers and cellular telephones.

There are several useful books which describe the physics of quartz crystal oscillators and other microresonators and their use in electronic circuits. For example, *Introduction to Quartz Crystal Unit Design* by Bottom, Van Nostrand Reinhold, New York, 1982, discusses the physical crystallography of quartz, mechanic vibrations and stress/strain relationships, the piezoelectric effect, the equivalent circuit of the quartz resonator and its use as a circuit component, the temperature stability of quartz oscillators, and other topics of importance in the application of these devices. *Science*, Vol. 249, pages 1000–1007 (1990), by Ward et al., describes the converse piezoelectric effect and its use in in-situ interfacial mass detection, such as in thickness monitors for thin-film preparation and in chemical sensors for trace gases. *Analytical Chemistry*, Vol. 65, pages 940A–948A and 987A–996A (1993), by Grate et al., compares the acoustical and electrical properties of five acoustic wave devices used as microsensors and transducers, including quartz crystal oscillators.

Any crystalline solid can undergo mechanical vibrations with minimum energy input at a series of resonant frequencies, determined by the shape and size of the crystal and by its elastic constants. In quartz, such vibrations can be induced by the application of a radio frequency voltage at the mechanical resonant frequency across electrodes attached to the crystal. This is termed the inverse piezoelectric effect. The thickness shear mode is the most common mechanical vibration used in quartz crystal oscillators. A typical commercially available quartz crystal oscillator is a thin circular quartz plate, cut from a single crystal at an angle of 37.25° C. with respect to the crystal's z axis (the so-called "AT cut"). This angle is chosen so that the temperature coefficient of the change in frequency is, to the first approximation, zero at 25° C., thus minimizing the drift in resonant frequency with ambient temperature change. A slight change in the cut angle produces crystals with zero temperature coefficients at elevated temperatures. The AT-cut plate has thin film electrodes on most of the top and bottom surfaces of the crystal, and is supported in various ways at its circumference or perimeter. Both the fundamental and the first few overtones of the thickness shear mode have been utilized in crystal oscillators. A typical AT-cut quartz disk piezoid operating at a 10.8 MHz fundamental has the following dimensions, according to page 99 of the above-mentioned reference by Bottom:

diameter: 8.0 mm electrode diameter: 2.5 mm blank thickness: 0.154 mm

The quality factor, Q, defined for any resonant circuit incorporating quartz crystal oscillators is usually not less than $10^5$ and may be as high as $10^7$. With careful attention to the control of temperature in a vacuum environment, a short-term frequency stability of one part in $10^{10}$ can be obtained, although the stated short-term stability for commercial units is ±3 ppm.

The resonant frequency of a quartz crystal oscillator is inversely proportional to the thickness, e, of the plate. For a circular disk, $f = nK/e$ where $n=1, 3, 5, \ldots$ and K is the frequency constant (for example, see page 134ff of the above-mentioned reference by Bottom). For an AT-cut disk, K=1664 kHz•mm, so that a disk of a thickness of 1 mm will oscillate at 1.664 MHz. If this thickness is increased by the deposition of material on the surface of the quartz crystal oscillator, then its frequency will decrease.

In 1957, Sauerbrey in *Z. Physik*, Vol. 155, 206 (1959), derived the fractional decrease in frequency Δf of a circular disk quartz crystal oscillator upon deposition of a mass, Δm, of material on its surface. The derivation relies on the assumption that a deposited foreign material exists entirely at the anti-node of the standing wave propagating across the thickness of the quartz crystal, so that the foreign deposit can be treated as an extension of the crystal, as, for example, described in *Applications of Piezoelectric Quartz Crystal Microbalances* by Lu et al., Elsevier, New York, 1984. Sauerbrey's result for the fundamental vibrational mode is as follows:

$$\Delta f/f_0 = -\Delta e/e_0 = -2f_0 \Delta m / A\sqrt{\rho \mu}$$

Here, $\Delta e$ is the change in the original thickness $e_0$, A is the piezoelectrically active area, $\rho$ is the density of quartz, and $\mu$ is the shear modulus of quartz. By measuring the decrease in frequency, one thus can determine the mass of material deposited on the crystal. This is the principle of the quartz crystal microbalance. In practice, the assumptions underlying the Sauerbrey equation are valid for deposits up to 10% of the crystal mass, although the sensitivity to mass has been shown experimentally to decrease from the center of the electrode to its edge.

Torres et al. in *J. Chem. Ed.*, Vol. 72, pages 67–70 (1995), describe the use of a quartz crystal microbalance to measure the mass effusing from Knudsen effusion cells at varying temperatures, in order to determine the enthalpies of sublimation. They reported a sensitivity of about $10^{-8}$ g/sec in the mass deposition rate. The application of the quartz crystal microbalance and other microresonators in chemistry for the sensitive detection of gases adsorbed on solid absorbing surfaces has been reviewed by Alder et al., in *Analyst*, Vol.

108, pages 1169–1189 (1983) and by McCallum in *Analyst*, Vol. 114, pages 1173–1189 (1989). The quartz crystal microbalance principle has been applied to the development of thickness monitors in the production of thin films by vacuum evaporation, as, for example, described in the above-mentioned reference by Lu et al. Quartz crystal oscillators of various sizes and modes of vibration are commonly used currently in research efforts in sensor development.

Throughout this application, various publications and patents are referred to by an identifying citation. The disclosures of the publications and patents referenced in this application are hereby incorporated by reference into the present disclosure to more fully describe the state of the art to which this invention pertains.

U.S. Pat. No. 5,339,051 to Koehler et al. describes resonator-oscillators for use as sensors in a variety of applications. U.S. Pat. Nos. 4,596,697 to Ballato and 5,151,110 to Bein et al. describe coated resonators for use as chemical sensors.

To overcome the influences of temperature changes on the microresonators, U.S. Pat. Nos. 4,561,286 to Sekler et al. and 5,476,002 to Bower et al. describe active temperature control or the use of temperature sensors with the microresonators. U.S. Pat. No. 5,686,779 to Vig describes a microresonator for direct use as a thermal sensor.

Microresonators, including quartz crystal microbalances (QCM's), have been utilized to determine the mass changes with a variety of liquid samples such as, for example, described in U.S. Pat. No. 4,788,466 to Paul et al. When the microresonator is coated, chemicals present in the liquid samples may be detected as, for example, described in U.S. Pat. No. 5,306,644 to Myerholtz et al.

Microresonators have been adapted to measure the viscosity of a liquid sample as, for example, described in U.S. Pat. No. 4,741,200 to Hammerle. U.S. Pat. No. 5,201,215 to Granstaff et al. describes the use of microresonators to measure the mass of a solid and physical properties of a fluid in a sample.

Calorimeters for various types of heat measurements are well known as, for example, described in U.S. Pat. No. 4,492,480 to Wadsö et al.; U.S. Pat. No. 5,295,745 to Cassettari et al.; and 5,312,587 to Templer et al. A combined scientific apparatus of a thermal analyzer, such as a calorimeter, and an X-ray diffractometer for observing simultaneously both thermodynamic and structural properties of materials is described in U.S. Pat. No. 4,821,303 to Fawcett et al.

Despite the various approaches proposed for the design of sensors based on microresonators as the sampling device, there remains a need for sensors which can simultaneously and continuously measure with high sensitivity and accuracy both mass and heat flow changes of a sample in contact with the microresonator.

SUMMARY OF THE INVENTION

One aspect of the present invention pertains to a new scientific instrument or device based on the combination of: (i) a microresonator, such as, for example, a quartz crystal microbalance (QCM), which may be used to measure very small changes of mass at its surface; and, (ii) a heat flow sensor, such as, for example, an isothermal heat conduction calorimeter (HCC), which may be used to measure small heat flows. In one embodiment, the microresonator and heat flow sensor combination measures simultaneously and continuously, with high sensitivity (nanogram in mass, submicrowatt in heat flow), the changes in mass and heat flow at a small gas-solid interface, for example, about 1 $cm^2$ or less in area, due to a chemical process such as evaporation or condensation, adsorption or desorption, or gas-surface reactions. The new scientific device of the present invention may be advantageously utilized in a variety of applications such as, for example, studying the hydration and dehydration of films of proteins and other biomolecules deposited on solid substrates, particularly for films utilized in biosensors, diagnostic immunoassays, the separation of proteins by chromatography, and as models for biological and biocompatible membranes and surfaces; studying the energetics of intermolecular interactions at the surface of polymer films and other organic surfaces important in adhesion, lubrication, wetting, and corrosion; and studying the energetics of the drying and curing of both water-based and organic solvent-based paints and finishes.

One aspect of the present invention pertains to a mass and heat flow measurement sensor comprising (i) a microresonator comprising a piezoelectric substrate having a perimeter, a first face for directly contacting a sample, and a second opposite face isolated from contacting the sample, the piezoelectric substrate having a resonant frequency and capable of producing a measurement signal based on the resonant frequency; (ii) a heat flow sensor coupled thermally to the piezoelectric substrate of the microresonator; and, (iii) a heat sink coupled thermally to the heat flow sensor. In one embodiment, the microresonator has the capability to measure the mass of the sample applied to the first face, and the heat flow sensor has the capability to measure the flow of heat from the sample on the first face of the microresonator to the heat sink.

Suitable microresonators for the sensors of this invention include, but are not limited to, bulk acoustic wave sensors, quartz crystal microbalances, surface acoustic wave sensors, flexural plate wave sensors, and acoustic plate mode sensors. In a preferred embodiment, the microresonator is a quartz crystal microbalance.

Another aspect of the present invention pertains to a mass and heat flow measurement sensor comprising (i) a microresonator comprising a piezoelectric substrate having a perimeter, a first face for directly contacting a sample, and a second opposite face isolated from contacting the sample; (ii) electrodes deposited on the first and second opposite faces of the piezoelectric substrate, the electrodes being capable of supplying electrical signals to and from the piezoelectric substrate; (iii) a heat flow sensor; (iv) a heat conductive material extending in a continuous fashion from the perimeter of the piezoelectric substrate to a first surface of the heat flow sensor, wherein the heat conductive material is not in contact with an acoustically active region of the second opposite face; and, (v) a heat sink material in contact to a second surface of the heat flow sensor, which second surface is not in direct contact with the heat conductive material. In one embodiment, the microresonator has the capability to measure the mass of the sample applied to the first face, and the heat flow sensor has the capability to measure the flow of heat from the sample on the first face of the microresonator to the heat sink. In a preferred embodiment, the heat flow sensor comprises a thermopile.

In one embodiment of the sensors of this invention, the piezoelectric substrate is a heat conductive material. In one embodiment, the piezoelectric substrate is a quartz crystal, and, preferably, the piezoelectric substrate is an AT-cut quartz crystal.

In one embodiment of the sensors of the present invention, the heat conductive material provides a path for the application of radio-frequency power to the piezoelectric substrate. In one embodiment, the heat conductive material comprises a metallic cylinder with a surface in contact to the first surface of the heat flow sensor. In one embodiment, the heat conductive material is brass.

One aspect of the present invention pertains to a mass and heat flow measurement sensor comprising (i) a quartz crystal microbalance capable of measuring the mass of a sample in contact with the quartz crystal microbalance; (ii) a heat flow sensor coupled thermally to the quartz crystal microbalance and capable of measuring the flow of heat from the sample to a heat sink; and, (iii) a heat sink coupled thermally to the heat flow sensor. In one embodiment, the quartz crystal microbalance comprises a quartz substrate having a perimeter, a first face for directly contacting the sample, and a second opposite face isolated from contacting the sample, the quartz substrate having a resonant frequency and capable of producing a measurement signal based on the resonant frequency. In one embodiment, the mass and heat flow measurement sensor further comprises electrodes deposited on the first and second opposite faces of the quartz substrate, the electrodes being capable of supplying electrical signals to and from the quartz substrate. In one embodiment, a heat conductive material extends in a continuous fashion from the perimeter of the quartz substrate to a first surface of the heat flow sensor, wherein the heat conductive material is not in contact with an acoustically active region of the second opposite face. In a preferred embodiment, the heat flow sensor comprises a thermopile. In one embodiment, the heat sink material is in contact to a second surface of the heat flow sensor, which second surface is not in direct contact with the heat conductive material. In a preferred embodiment, the quartz substrate is an AT-cut quartz crystal. In one embodiment, the heat conductive material provides a path for the application of radio-frequency power to the quartz substrate. In one embodiment, the heat conductive material comprises a metallic cylinder with a surface in contact to the first surface of the heat flow sensor. In one embodiment, the heat conductive material is brass.

Another aspect of the present invention relates to methods for measuring the mass of a sample and the flow of heat from the sample to a heat sink, which methods comprise the steps of: (i) providing a microresonator, as described herein; (ii) providing a heat flow sensor coupled thermally to the piezoelectric substrate of the microresonator; (iii) providing a heat sink coupled thermally to the heat flow sensor; and, (iv) measuring the changes in mass of the sample and the flow of heat from the sample to the heat sink for the sample disposed on the first face of the piezoelectric substrate.

Still another aspect of the present invention relates to methods for measuring the mass of a sample and the flow of heat from the sample to a heat sink, which methods comprise the steps of: (i) providing a microresonator, as described herein, (ii) providing electrodes deposited on the first and second opposite faces of the piezoelectric substrate, the electrodes being capable of supplying electrical signals to and from the piezoelectric substrate; (iii) providing a heat flow sensor, as described herein; (iv) providing a heat conductive material extending in a continuous fashion from the perimeter of the piezoelectric substrate to a first surface of the heat flow sensor, wherein the heat conductive material is not in contact with an acoustically active region of the second opposite face; (v) providing a heat sink material in contact to a second surface of the heat flow sensor, which second surface is not in direct contact with the heat conductive material; and, (vi) measuring the changes in mass of the sample and the flow of heat from the sample to the heat sink for the sample disposed on the first face of the piezoelectric substrate. In one embodiment, the microresonator has the capability to measure the mass of the sample applied to the first face, and the heat flow sensor has the capability to measure the flow of heat from the sample on the first face of the microresonator to the heat sink.

Yet another aspect of the present invention relates to methods for measuring the mass of a sample and the flow of heat from the sample to a heat sink, which methods comprise the steps of: (i) providing a quartz crystal microbalance capable of measuring the mass of the sample in contact with the quartz crystal microbalance; (ii) providing a heat flow sensor coupled thermally to the quartz crystal microbalance and capable of measuring the flow of heat from the sample to a heat sink; (iii) providing a heat sink coupled thermally to the heat flow sensor; and, (iv) measuring the changes in mass of the sample and the flow of heat from the sample to the heat sink for the sample disposed on the quartz crystal microbalance. In one embodiment of the methods, the quartz crystal microbalance comprises a quartz substrate having a perimeter, a first face for directly contacting the sample, and a second opposite face isolated from contacting the sample, the quartz substrate having a resonant frequency and capable of producing a measurement signal based on the resonant frequency. In one embodiment, the methods further comprise providing electrodes deposited on the first and second opposite faces of the quartz substrate, the electrodes being capable of supplying electrical signals to and from the quartz substrate. In one embodiment, the methods further comprise providing a heat conductive material extending in a continuous fashion from the perimeter of the quartz substrate to a first surface of the heat flow sensor, wherein the heat conductive material is not in contact with an acoustically active region of the second opposite face. In a preferred embodiment, the heat flow sensor comprises a thermopile. In one embodiment, the heat sink material is in contact to a second surface of the heat flow sensor, which second surface is not in direct contact with the heat conductive material. In a preferred embodiment, the quartz substrate is an AT-cut quartz crystal. In one embodiment, the heat conductive material provides a path for the application of radio-frequency power to the quartz substrate. In one embodiment, the heat conductive material comprises a metallic cylinder with a surface in contact to the first surface of the heat flow sensor. In one embodiment, the heat conductive material is brass.

As one skilled in the art will appreciate, features of one embodiment and aspect of the invention are applicable to other embodiments and aspects of the invention.

BRIEF DESCRIPTION OF THE DRAWINGS

The foregoing summary, as well as the following detailed description of embodiments of the invention, will be better understood when read in conjunction with the appended drawings. For the purpose of illustrating the invention, particular arrangements and methodologies are shown in the drawings. It should be understood, however, that the invention is not limited to the precise arrangements shown or to the methodologies of the detailed description.

DETAILED DESCRIPTION OF THE INVENTION

The microresonator and heat flow sensor combination of the present invention provides a new method in thermal analysis and calorimetry. This new method provides the capability of measuring the change in heat flow and mass at a gas-solid interface as the compositions of both the gas phase and the solid surface change. In thermodynamic terms, the microresonator and heat flow combination is capable of measuring directly the partial molal enthalpy of a volatile component, i, of a film on a surface, as the other non-volatile components and the temperature (T) and pressure (P) are held constant:

$$H_i = (\partial H / \partial n_i)_{T,P,nj}$$

where j is the number of moles of the total components (n).

Figure 1:
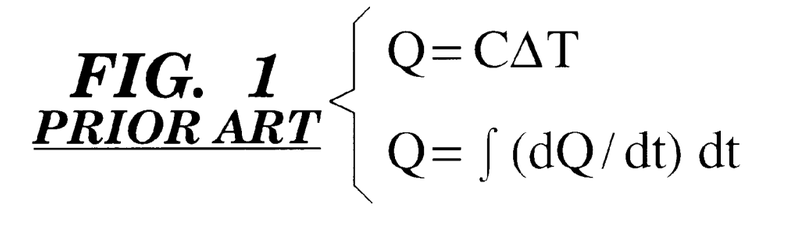
FIG. 1 illustrates the contrast between the functionality of an adiabatic calorimeter versus a heat conduction calorimeter.
Figure 2:
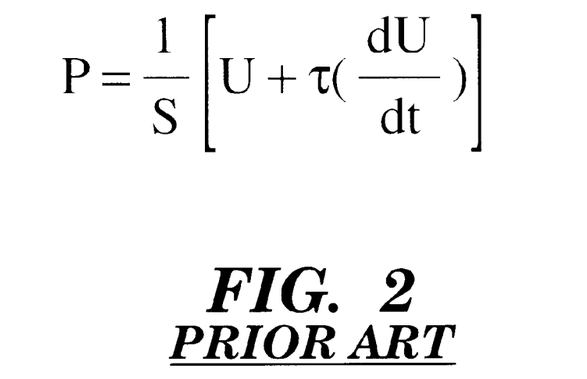
FIG. 2 shows the basic equations for heat conduction calorimetry.
Figure 3:
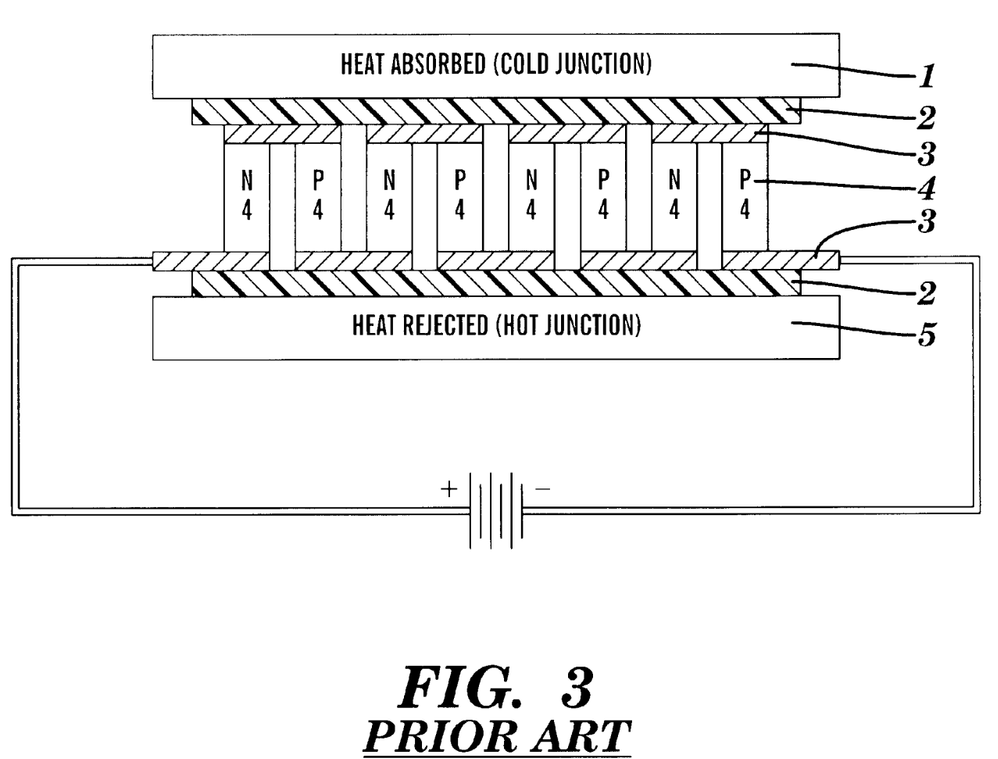
FIG. 3 shows a schematic representation of a typical thermoelectric thermopile module.

The contrast between adiabatic calorimetry and heat conduction calorimetry is illustrated in FIG. 1. For adiabatic calorimetery, the temperature (T) vs. time is measured in an adiabatic vessel of known heat capacity (C) to provide the heat (Q). For heat conduction calorimetry, the thermal power vs. time (t) is measured in a vessel in which the heat (Q) generated by the chemical process flows through a heat flow sensor. The basic equations for heat conduction calorimetry or "Calvet calorimetry" are shown in FIG. 2, where P is the thermal power in watts, S is the thermopile sensitivity in volts/watt, U is the thermopile voltage in volts, and $\tau$ is the time constant of the calorimeter in seconds. At steady state, U=SP. The time constant is determined by C/G, where C is the heat capacity of the reaction vessel and G is the thermal conductance of the thermopile. The sensing element in a heat flow sensor is typically a thermopile, or thermoelectric, module. Examples of these thermopile modules are manufactured by Melcor, Inc., of Trenton, N.J., and are widely used as thermoelectric heat pumps in computers and other electronics. FIG. 3 shows some design details of a typical thermoelectric thermopile, as, for example, those made by Melcor, Inc. The top layer 1 of the assembly is a cold junction where heat is absorbed. The electrical insulator layer 2 and electrical conductor layer 3 are on both sides of bismuth telluride elements 4 with "N" and "P" type properties. The bottom layer 5 of the assembly is a hot junction where heat is rejected. The elements are electrically connected in series through a direct current (dc) source and are thermally in parallel. In practical use, couples are combined in a module where they are connected electrically in series, and thermally in parallel. Normally a module is the smallest component commercially available. Modules are available in a great variety of sizes, shapes, operating currents, operating voltages, and ranges of heat pumping capacity.

Mass and Heat Flow Measurement Sensors

Figure 4:
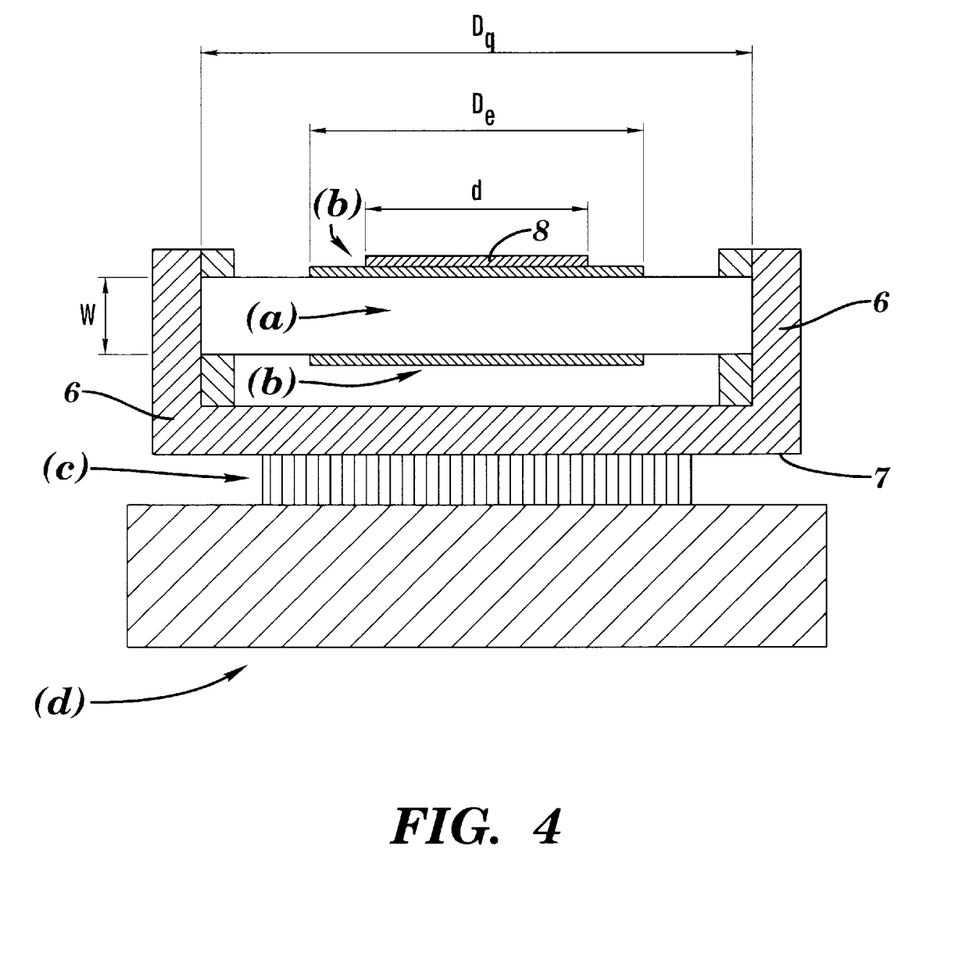
FIG. 4 shows a schematic representation of a quartz crystal microbalance and heat flow sensor combination in accordance with one embodiment of the present invention.

A schematic diagram of one aspect of the microresonator and heat flow sensor combination of the present invention is shown in FIG. 4. As illustrated in FIG. 4, a circular disk, (a), of an AT-cut quartz crystal of diameter, $D_q$, and thickness, w, is mounted with its circumferential edge or perimeter in good thermal contact to a metallic cylinder 6 with a bottom plate 7. The disk has electrodes (b) of diameter, $D_e$, deposited on both faces. The bottom plate is in contact to a thermopile (c), which is in turn in contact to a heat sink (d), for example, the bottom of a can which is thermostated in a constant temperature bath. Thus, the heat flow sensor comprising the thermopile is coupled thermally to the microresonator, and the heat sink is coupled thermally to the heat flow sensor. On the top surface or first face of the quartz crystal oscillator with electrode is deposited a sample 8 in a circular area of diameter, d. It is this sample which will produce a heat flow rate, $\phi$ (watts), when, for example, subliming, adsorbing, desorbing, or reacting at a rate of dn/dt moles per second, where the symbol, $\Delta H_{sub}$, is used to represent the enthalpy change of any of the processes mentioned above and $\phi = \Delta H_{sub} \, dn/dt$. For example, a typical sublimation enthalpy of 50 kJ mol$^{-1}$, combined with a heat flow rate of 100 nW typical of the baseline noise in a good heat conduction microcalorimeter, corresponds to a sublimation rate, dn/dt, of $5.0 \times 10^{-12}$ mole sec$^{-1}$. For a substance of molar mass of 200 g mol$^{-1}$, this corresponds to a mass loss of 1.0 ng sec$^{-1}$. The Nanowatt Amplifier available from Thermometric AB in Sweden, as described in *Thermometric Calorimeter News*, February 1997, page 3, with a noise level for an empty ampoule heat conduction calorimeter of 2 nW, will increase this sensitivity by a factor of 50, or to $1.0 \times 10^{-13}$ mole sec$^{-1}$ (20 pg sec$^{-1}$). The bottom surface or opposite face of the quartz crystal with electrodes is isolated from contacting the sample.

One aspect of the present invention pertains to a mass and heat flow measurement sensor comprising (i) a microresonator comprising a piezoelectric substrate having a perimeter, a first face for directly contacting a sample, and a second opposite face isolated from contacting the sample, the piezoelectric substrate having a resonant frequency and capable of producing a measurement signal based on the resonant frequency; (ii) a heat flow sensor coupled thermally to the piezoelectric substrate of the microresonator; and, (iii) a heat sink coupled thermally to the heat flow sensor. In one embodiment, the microresonator has the capability to measure the mass of the sample applied to the first face, and the heat flow sensor has the capability to measure the flow of heat from the sample on the first face of the microresonator to the heat sink.

A wide variety of microresonators may be utilized in the mass and heat flow measurement sensors of the present invention as, for example, the microresonators described in the afore-mentioned references by Grate et al., Alder et al., McCullen, and Lu et al. Suitable microresonators for the sensors of this invention include, but are not limited to, bulk acoustic wave sensors, quartz crystal microbalances, surface acoustic wave sensors, flexural plate wave sensors, and acoustic plate mode sensors. In a preferred embodiment, the microresonator is a quartz crystal microbalance. A wide variety of heat flow sensors may be utilized in the mass and heat flow measurement sensors of the present invention, such as, for example, the isothermal heat conduction calorimeters described in *Chemical Society Reviews*, Volume 1997, pages 79–86 (1997) by Wadsö and references therein.

A key requirement in the microresonator and heat flow sensor combination of the present invention is to provide a path of high thermal conductivity from the piezoelectric crystal surface to the heat flow sensor. Otherwise, at high heat flow rates, the central portion of the piezoelectric crystal surface may heat up, thus producing temperature gradients within the crystal and accompanying shifts in resonant frequency. There must be good thermal contact between the piezoelectric crystal and the mounting of the thermally conductive material, so the details of mechanical support are important. In Chapter 10 of the above-mentioned reference by Bottom, it is shown that the quartz between the two circular deposited electrodes is the region undergoing transverse shear waves, and that the surrounding bare quartz annulus serves to damp higher acoustic modes. To the first approximation, the annulus functions as an acoustical node. It is therefore available to mount the crystal and make a path of high thermal conductivity between the piezoelectric substrate and the heat flow sensor without affecting the high quality factor, Q, of acoustical vibrations at resonance. FIG. 4 shows one possible mounting arrangement of the microresonator and heat flow sensor combination of the present invention. The heat conductive material providing the high thermal conductivity between the piezoelectric substrate and the heat flow sensor is not in contact with the acoustically active region undergoing transverse shear waves, including the acoustically active region on the opposite face of the piezoelectric crystal.

It is possible to estimate the temperature gradient in the quartz between the two electrodes under operating conditions for a microresonator comprising a quartz crystal.

The radial temperature distribution, T(r), in a disk of diameter, $D_e$, and thickness, c, connected to a heat sink of temperature, $T_0$, at its edge and uniformly heated on its surface with an input power per unit area, P, has been derived by Ginnings et al., in "Principles of Calorimetric Design" in *Experimental Thermodynamics: Calorimetry of Non-Reacting Systems*, Vol. 1, edited by McCullough et al., Butterworth, London, 1968, as follows:

$$T(r)-T_0=P/4\lambda e[D_e^2/4-r^2]$$

where $\lambda$ is the thermal conductivity of the disk material. Thermal conductivity in quartz is anisotropic. For heat flow along the C-axis (the optical axis), $\lambda=11.1$ W $K^{-1}m^{-1}$, whereas for a perpendicular axis, $\lambda=5.88$ W $K^{-1}m^{-1}$. To estimate temperature gradients, we take the mean, $\lambda=8.5$ W $K^{-1}m^{-1}$, and use the dimensions given above ($D_e=0.0025$ m, e=0.000154 m, or electrode area=$4.91\times10^{-6}$ $m^2$). Assuming a heat flow of 100 $\mu$W, or $10^3$ times the noise level of the microcalorimeter, the temperature difference between the center of the disk and the edge of the electrode ($r=D_e$) is only $6\times10^{-3}$ K, independent of disk diameter. This is much too small to create effects due to the dependence of quartz resonant frequency on temperature. Thus, for example, quartz is an adequate thermal conductor to function in the microresonator and heat flow sensor combination of the present invention.

Another aspect of the present invention pertains to a mass and heat flow measurement sensor comprising (i) a microresonator comprising a piezoelectric substrate having a perimeter, a first face for directly contacting a sample, and a second opposite face isolated from contacting the sample; (ii) electrodes deposited on the first and second opposite faces of the piezoelectric substrate, the electrodes being capable of supplying electrical signals to and from the piezoelectric substrate; (iii) a heat flow sensor; (iv) a heat conductive material extending in a continuous fashion from the perimeter of the piezoelectric substrate to a first surface of the heat flow sensor, wherein the heat conductive material is not in contact with an acoustically active region of the second opposite face; and, (v) a heat sink material in contact to a second surface of the heat flow sensor, which second surface is not in direct contact with the heat conductive material. In one embodiment, the microresonator has the capability to measure the mass of the sample applied to the first face, and the heat flow sensor has the capability to measure the flow of heat from the sample on the first face of the microresonator to the heat sink. In a preferred embodiment, the heat flow sensor comprises a thermopile.

In one embodiment of the sensors of this invention, the piezoelectric substrate is a heat conductive material. In one embodiment, the piezoelectric substrate is a quartz crystal, and, preferably, the piezoelectric substrate is an AT-cut quartz crystal.

In one embodiment of the sensors of the present invention, the heat conductive material provides a path for the application of radio-frequency power to the piezoelectric substrate. In one embodiment, the heat conductive material comprises a metallic cylinder with a surface in contact to the first surface of the heat flow sensor. In one embodiment, the heat conductive material is brass.

For the embodiment shown in FIG. 4, the "reaction vessel" of the microresonator and heat flow sensor of this invention has a small heat capacity and thus a short time constant, as, for example, described in *J. Biochemical and Biophysical Methods*, Vol. 28, pages 85–100 (1994), by Backman et al. This short time constant may perhaps be as short as a few seconds. This makes less demands on the long-term stability of both the microresonator and the heat flow sensor and the temperature stability of the heat sink. The short time constant will also be useful in following the kinetics of adsorption or desorption of materials. The operating frequency of the microresonator should be high enough to assure good counting statistics in the frequency measurement, but high frequencies imply thin quartz crystals and a corresponding fragility and a decrease in thermal conductivity. The width, w, of the microresonator is a design parameter to be determined by optimizing these conflicting requirements.

As shown in FIG. 4, one embodiment of the microresonator and heat flow sensor of the present invention is a single device incorporating one microresonator, such as a quartz crystal microbalance, and one heat flow sensor comprising a thermopile for mass and heat flow measurements. Calibration of the heat flow thermopile is accomplished, for example, by shining a 1.0 milliwatt He—Ne laser onto the microresonator of the microresonator and heat flow sensor combination and measuring the resulting heat flow sensor voltage. When 5.0 MHz of radio-frequency (rf) power is supplied to the piezoelectric quartz crystal of the microresonator, the heat generated can be detected by the heat flow sensor.

As illustrated in one embodiment in FIG. 4, one aspect of the present invention pertains to a mass and heat flow measurement sensor comprising (i) a quartz crystal microbalance capable of measuring the mass of a sample in contact with the quartz crystal microbalance; (ii) a heat flow sensor coupled thermally to the quartz crystal microbalance and capable of measuring the flow of heat from the sample to a heat sink; and, (iii) a heat sink coupled thermally to the heat flow sensor. In one embodiment, the quartz crystal microbalance comprises a quartz substrate having a perimeter, a first face for directly contacting the sample, and a second opposite face isolated from contacting the sample, the quartz substrate having a resonant frequency and capable of producing a measurement signal based on the resonant frequency. In one embodiment, the mass and heat flow measurement sensor further comprises electrodes deposited on the first and second opposite faces of the quartz substrate, the electrodes being capable of supplying electrical signals to and from the quartz substrate. In one embodiment, a heat conductive material extends in a continuous fashion from the perimeter of the quartz substrate to a first surface of the heat flow sensor, wherein the heat conductive material is not in contact with an acoustically active region of the second opposite face. In a preferred embodiment, the heat flow sensor comprises a thermopile. In one embodiment, the heat sink material is in contact to a second surface of the heat flow sensor, which second surface is not in direct contact with the heat conductive material. In a preferred embodiment, the quartz substrate is an AT-cut quartz crystal. In one embodiment, the heat conductive material provides a path for the application of radio-frequency power to the quartz substrate. In one embodiment, the heat conductive material comprises a metallic cylinder with a surface in contact to the first surface of the heat flow sensor. In one embodiment, the heat conductive material is brass.

The expected detection limits of the heat flow and mass change measurements of the microresonator and heat flow sensor combination may be estimated. For a microresonator, such as a quartz crystal microbalance, the frequency shift, δυ, is related to the mass change per unit area, δm, deposited on the microresonator surface by the Sauerbrey equation, which for the embodiment of a quartz crystal microbalance shown in FIG. 4, can be expressed as:

$$\delta\upsilon = -57\delta m$$

where the frequency shift is in Hz and the mass change is in micrograms/cm$^2$. Since the observed short-term stability of the quartz crystal microbalance is about ±1 Hz in its present configuration, the mass detection limit is presently about 18 ng/cm$^2$. With better counting electronics, this limit could be reduced by at least an order of magnitude. The sensitivity of the heat flow sensor is about 0.3 V/W, so the observed rms noise in the heat flow sensor output channel of ±1 microvolt corresponds to a heat conduction detection limit of 3 microwatts.

Methods for Measuring Mass and Heat Flow of Samples

One aspect of the present invention relates to methods for measuring the mass of a sample and the flow of heat from the sample to a heat sink, which methods comprise the steps of: (i) providing a microresonator, as described herein; (ii) providing a heat flow sensor coupled thermally to the piezoelectric substrate of the microresonator; (iii) providing a heat sink coupled thermally to the heat flow sensor; and, (iv) measuring the changes in mass of the sample and the flow of heat from the sample to the heat sink for the sample disposed on the first face of the piezoelectric substrate.

As described herein, in the sensors and methods of the present invention, the change in mass of the sample is measured by a change in the frequency of the piezoelectric substrate of the microresonator, and the change in the flow of heat from the sample to the heat sink is typically measured by a change in the voltage output of the heat flow sensor. Suitable electrical circuitry and data collection and correlation equipment and methods for these measurements include, but are not limited to, those described for microresonators in the afore-mentioned references by Grate et al., Alder et al., McCallum, and Lu et al., and for heat flow sensors in the afore-mentioned review article by Wadsö and references therein.

Another aspect of the present invention relates to methods for measuring the mass of a sample and the flow of heat from the sample to a heat sink, which methods comprise the steps of: (i) providing a microresonator, as described herein, (ii) providing electrodes deposited on the first and second opposite faces of the piezoelectric substrate, the electrodes being capable of supplying electrical signals to and from the piezoelectric substrate; (iii) providing a heat flow sensor, as described herein; (iv) providing a heat conductive material extending in a continuous fashion from the perimeter of the piezoelectric substrate to a first surface of the heat flow sensor, wherein the heat conductive material is not in contact with an acoustically active region of the second opposite face; (v) providing a heat sink material in contact to a second surface of the heat flow sensor, which second surface is not in direct contact with the heat conductive material; and, (vi) measuring the changes in mass and the flow of heat from the sample to the heat sink for the sample disposed on the first face of the piezoelectric substrate. In one embodiment, the microresonator has the capability to measure the mass of the sample applied to the first face, and the heat flow sensor has the capability to measure the flow of heat from the sample on the first face of the microresonator to the heat sink.

As illustrated in one embodiment in FIG. 4, yet another aspect of the present invention relates to methods for measuring the mass of a sample and the flow of heat from the sample to a heat sink, which methods comprise the steps of: (i) providing a quartz crystal microbalance capable of measuring the mass of the sample in contact with the quartz crystal microbalance; (ii) providing a heat flow sensor coupled thermally to the quartz crystal microbalance and capable of measuring the flow of heat from the sample to a heat sink; (iii) providing a heat sink coupled thermally to the heat flow sensor; and, (iv) measuring the changes in mass of the sample and the flow of heat from the sample to the heat sink for the sample disposed on the quartz crystal microbalance. In one embodiment of the methods, the quartz crystal microbalance comprises a quartz substrate having a perimeter, a first face for directly contacting the sample, and a second opposite face isolated from contacting the sample, the quartz substrate having a resonant frequency and capable of producing a measurement signal based on the resonant frequency. In one embodiment, the methods further comprise providing electrodes deposited on the first and second opposite faces of the quartz substrate, the electrodes being capable of supplying electrical signals to and from the quartz substrate. In one embodiment, the methods further comprise providing a heat conductive material extending in a continuous fashion from the perimeter of the quartz substrate to a first surface of the heat flow sensor, wherein the heat conductive material is not in contact with an acoustically active region of the second opposite face. In a preferred embodiment, the heat flow sensor comprises a thermopile. In one embodiment, the heat sink material is in contact to a second surface of the heat flow sensor, which second surface is not in direct contact with the heat conductive material. In a preferred embodiment, the quartz substrate is an AT-cut quartz crystal. In one embodiment, the heat conductive material provides a path for the application of radio-frequency power to the quartz substrate. In one embodiment, the heat conductive material comprises a metallic cylinder with a surface in contact to the first surface of the heat flow sensor. In one embodiment, the heat conductive material is brass.

Applications of the Microresonator and Heat Flow Sensor Combination to Measure Enthalpies of Sublimation In his review of trends in isothermal microcalorimetry in *Chemical Society Reviews*, Volume 1997, pages 79–86 (1997), Wadsö states:

"There is a strong need for enthalpy of sublimation data for substances with very low vapor pressures, for example in connection with investigations of biothermodynamic model systems. However, very little development work and few measurements have been reported during the last few decades in vaporization/sublimation calorimetry. More advanced microcalorimetric techniques are much needed in this field."

Isothermal heat conduction calorimetry has been used to measure $\Delta H_{sub}$ for compounds with vapor pressures as low as $10^{-6}$ torr, as, for example, described in *Chemical Scripta*, Vol. 1, pages 103–111 (1971) by Morawetz and in *Thermochimica Acta*, Vol. 115, pages 153–165 (1987) by Sabbah et al. Knudsen effusion methods, which use the Clausius-Clapeyron equation to derive $\Delta H_{sub}$ from the variation of vapor pressure with temperature, as, for example, described in *J. Chem. Thermo.*, Vol. 27, pages 1261–1266 (1995) by Torres et al., have been used on compounds with vapor pressures in the same range. Because many interesting organic and biological substances have room temperature vapors lower than these limits, their enthalpies of sublimation have not yet been measured. Yet for an accurate determination of the Gibbs free energy of formation, the heat of sublimation must be known. The energetics of formation of such substances in the gas phase is of great importance in determining the chemical reactivity of the substance, and in comparing with quantum chemical calculations of the same quantity.

The microresonator and heat flow sensor combination of the present invention can be used to measure sublimation enthalpies of quite non-volatile materials. The relationship between the sublimation rate of a solid, $\sigma$(moles $m^{-2}s^{-1}$), and its vapor pressure was first presented by Langmuir in *Physical Review*, Vol. 2, 329 (1913), as follows:

$$\sigma = P_{eq}/\sqrt{2\pi MRT}$$

Here, $P_{eq}$ is the equilibrium vapor pressure of the solid, M is its molar mass, R is the gas constant, and T is the absolute temperature. For the hypothetical solid described above, with a sublimation enthalpy of 50 kJ/mol and a molar mass of 200 g/mole, a surface area of 1 $cm^2$ will lose mass at the rate of 1.0 ng/sec if the vapor pressure of the solid is $2.0 \times 10^{-8}$ torr.

From the design perspective, it is helpful to use as large a diameter, D, for the microresonator as possible, since this permits a larger sample area ($\pi d^2/4$ as shown in FIG. 4) and thus a larger thermal signal. Of importance in evacuating the microresonator and heat flow sensor combination of the present invention is the nature of the piezoelectric substrate-to-metal contact, such as quartz-to-metal contact, (for example, o-ring, direct contact without bonding, or a high-vacuum seal), since the underside of the quartz crystal must not be subject to adsorbing vapors from the sample.

Applications of the Microresonator and Heat Flow Sensor Combination to Energy-Sensitive Chemical Sensors There is a large and actively growing literature on specific and sensitive chemical sensors based on surface-coated microresonator, such as quartz crystal oscillator, technology. For example, *Sensors and Actuators B*, Vol. 18–19, pages 429–433 (1994) by Hartmann et al., describes use of a quartz crystal microbalance coated with polymers, with lipophilic compounds, with calix-n-arenes, with complex formers, and with a monomolecular layer to explore the sensitivity and selectivity of quartz crystal microbalance-based gas sensors. Also, for example, *Sensors and Actuators B*, Vol. 34, pages 356–360 (1996) by Zhou et al., describes coating both a quartz crystal microbalance and a separate calorimetric transducer with a cycloaliphatic poly(ether urethane) to detect organic solvent vapors. However, there has been no report of a combined microresonator and heat flow sensor combination used as a gas sensor. Since the combined microresonator and heat flow sensor combination of the present invention gives a real-time measurement of the molar heat of adsorption, it has a powerful additional measurement dimension which should provide further selectivity for gas sensors. There are also many fundamental problems of interest to study with the microresonator and heat flow sensor combination of this invention, such as, for example, the continuous variation in molar enthalpy with increasing surface coverage from adsorption of a monolayer to condensation of the bulk solid.

Applications of the Microresonator and Heat Flow Sensor Combination to Measuring the Binding Enthalpy of Water in Biological Materials If a protein in solution is coated on the microresonator, such as a quartz crystal microbalance, at high water vapor pressure or relative humidity, the decrease in mass and the heat required for evaporation of water may be studied by varying the partial pressure of water in the gas above the surface. At first, one should expect the thermal signal to be almost the same as the enthalpy of vaporization of water itself, but as more and more water is removed, the binding energy per water molecule should change to that more representative of protein molecule-water interaction energies. Such studies should help to elucidate the binding energetics of water in any biological material.

Other Applications of the Microresonator and Heat Flow Sensor Combination

The microresonator and heat flow sensor combination of the present invention measures simultaneously and continuously, with high sensitivity (nanogram in mass, sub-microwatt in heat flow), the change in mass and heat flow at a small gas-solid interface of, for example, about 1 $cm^2$, due to chemical processes such as evaporation or condensation, adsorption or desorption, or gas-surface reactions. Other potential applications of the microresonator and heat flow sensor combination of this invention include, but are not limited to, the study of:

(a) the hydration and dehydration of films of proteins and other biomolecules deposited on solid substrates. These films are used, for example, in biosensors, diagnostic immunoassays, the separation of proteins by chromatography, and as models for biological and biocompatible membranes and surfaces;

(b) the energetics of intermolecular interactions at the surface of polymer films and other organic surfaces important in adhesion, lubrication, wetting, and corrosion; and, (c) the energetics of the drying and curing of both water-based and organic solvent-based paints and finishes.

While the invention has been described in detail and with reference to specific embodiments thereof, it will be apparent to one skilled in the art that various changes and modifications can be made without departing from the spirit and scope thereof.

What is claimed is:

1. A mass and heat flow measurement sensor comprising:

(a) a microresonator comprising a piezoelectric substrate having a perimeter, a first face for directly contacting a sample, and a second opposite face isolated from contacting the sample, said piezoelectric substrate having a resonant frequency and capable of producing a measurement signal based on said resonant frequency;

(b) a heat flow sensor coupled thermally to the piezoelectric substrate of said microresonator; and, (c) a heat sink coupled thermally to said heat flow sensor.

2. The mass and heat flow measurement sensor of claim 1, wherein said microresonator is capable of measuring the mass of the sample applied to said first face, and further wherein said heat flow sensor is capable of measuring the flow of heat from the sample on said first face to the heat sink.

3. The mass and heat flow measurement sensor of claim 1, wherein said microresonator is selected from the group of microresonators consisting of:

bulk acoustic wave sensors, quartz crystal microbalances, surface acoustic wave sensors, flexural plate wave sensors, and acoustic plate mode sensors.

4. The mass and heat flow measurement sensor of claim 1, wherein said microresonator is a quartz crystal microbalance.

5. The mass and heat flow measurement sensor of claim 1, wherein said piezoelectric substrate operates in a thickness shear mode.

6. The mass and heat flow measurement sensor of claim 1, wherein said piezoelectric substrate is a quartz crystal.

7. The mass and heat flow measurement sensor of claim 1, wherein said piezoelectric substrate is an AT-cut quartz crystal.

8. A mass and heat flow measurement sensor comprising:

(a) a microresonator comprising a piezoelectric substrate having a perimeter, a first face for directly contacting a sample, and a second opposite face isolated from contacting the sample;

(b) electrodes deposited on the first and second opposite faces of said piezoelectric substrate, said electrodes being capable of supplying electrical signals to and from said piezoelectric substrate;

(c) a heat flow sensor;

(d) a heat conductive material extending in a continuous fashion from the perimeter of said piezoelectric substrate to a first surface of said heat flow sensor, wherein said heat conductive material is not in contact with an acoustically active region of said second opposite face; and, (e) a heat sink material in contact to a second surface of said heat flow sensor, which second surface is not in direct contact with said heat conductive material.

9. The mass and heat flow measurement sensor of claim 8, wherein said microresonator is capable of measuring the mass of the sample applied to said first face, and further wherein said heat flow sensor is capable of measuring the flow of heat from the sample on said first face to the heat sink.

10. The mass and heat flow measurement sensor of claim 8, wherein said heat flow sensor comprises a thermopile.

11. The mass and heat flow measurement sensor of claim 8, wherein said piezoelectric substrate operates in a thickness shear mode.

12. The mass and heat flow measurement sensor of claim 8, wherein said piezoelectric substrate is a heat conductive material.

13. The mass and heat flow measurement sensor of claim 8, wherein said piezoelectric substrate is a quartz crystal.

14. The mass and heat flow measurement sensor of claim 8, wherein said piezoelectric substrate is an AT-cut quartz crystal.

15. The mass and heat flow measurement sensor of claim 8, wherein said heat conductive material is capable of providing a path for the application of radio-frequency power to said piezoelectric substrate.

16. The mass and heat flow measurement sensor of claim 8, wherein said heat conductive material comprises a metallic cylinder with a surface in contact to the first surface of said heat flow sensor.

17. The mass and heat sensor of claim 8, wherein said heat conductive material is brass.

18. A mass and heat flow measurement sensor comprising:

(a) a quartz crystal microbalance capable of measuring the mass of a sample in contact with said quartz crystal microbalance; and, (b) a heat flow sensor coupled thermally to said quartz crystal microbalance and capable of measuring the flow of heat from the sample to a heat sink; and, (c) a heat sink coupled thermally to said heat flow sensor.

19. The mass and heat flow measurement sensor of claim 18, wherein said quartz crystal microbalance comprises a quartz substrate having a perimeter, a first face for directly contracting the sample, and a second opposite face isolated from contacting the sample, said quartz substrate having a resonant frequency and capable of producing a measurement signal based on said resonant frequency.

20. The mass and heat flow measurement sensor of claim 19, wherein said mass and heat flow measurement sensor further comprises electrodes deposited on the first and second opposite faces of said quartz substrate, said electrodes being capable of supplying electrical signals to and from said quartz substrate.

21. The mass and heat flow measurement sensor of claim 20, wherein a heat conductive material extends in a continuous fashion from the perimeter of said quartz substrate to a first surface of said heat flow sensor, wherein said heat conductive material is not in contact with an acoustically active region of said second opposite face.

22. The mass and heat flow measurement sensor of claim 21, wherein said heat flow sensor comprises a thermopile.

23. The mass and heat flow measurement sensor of claim 21, wherein said heat sink is in contact to a second surface of said heat flow sensor, which second surface is not in direct contact with said heat conductive material.

24. The mass and heat flow measurement sensor of claim 21, wherein said quartz substrate is an AT-cut quartz crystal.

25. The mass and heat flow measurement sensor of claim 21, wherein said heat conductive material is capable of providing a path for the application of radio-frequency power to said quartz substrate.

26. The mass and heat flow measurement sensor of claim 21, wherein said heat conductive material comprises a metallic cylinder with a surface in contact to the first surface of said heat flow sensor.

27. The mass and heat flow measurement sensor of claim 21, wherein said heat conductive material is brass.

28. A method for measuring the mass of a sample and the flow of heat from the sample to a heat sink, the method comprising the steps of:

(a) providing a microresonator which comprises a piezoelectric substrate having a perimeter, a first face for directly contacting a sample, and a second opposite face isolated from contacting the sample, said piezoelectric substrate having a resonant frequency and capable of producing a measurement signal based on said resonant frequency;

(b) providing a heat flow sensor coupled thermally to the piezoelectric substrate of said microresonator;

(c) providing a heat sink coupled thermally to said heat flow sensor; and (d) measuring the changes in mass of the sample and the flow of heat from the sample to the heat sink for the sample disposed on the first face of said piezoelectric substrate.

29. The method of claim 28, wherein said microresonator measures the mass of the sample applied to said first face, and further wherein said heat flow sensor measures the flow of heat from the sample on said first face to the heat sink.

30. The method of claim 28, wherein said microresonator is selected from the group of microresonators consisting of: bulk acoustic wave sensors, quartz crystal microbalances, surface acoustic wave sensors, flexural plate wave sensors, and acoustic plate mode sensors.

31. The method of claim 28, wherein said microresonator is a quartz crystal microbalance.

32. The method of claim 28, wherein said piezoelectric substrate operates in a thickness shear mode.

33. The method of claim 28, wherein said piezoelectric substrate is a quartz crystal.

34. The method of claim 28, wherein said piezoelectric substrate is an AT-cut quartz crystal.

35. A method for measuring the mass of a sample and the flow of heat from the sample to a heat sink, the method comprising the steps of:

(a) providing a microresonator which comprises a piezoelectric substrate having a perimeter, a first face for directly contacting a sample, and a second opposite face isolated from contacting the sample;

(b) providing electrodes deposited on the first and second opposite faces of said piezoelectric substrate, said electrodes being capable of supplying electrical signals to and from said piezoelectric substrate;

(c) providing a heat flow sensor;

(d) providing a heat conductive material extending in a continuous fashion from the perimeter of said piezoelectric substrate to a first surface of said heat flow sensor, wherein said heat conductive material is not in contact with an acoustically active region of said second opposite face;

(e) providing a heat sink material in contact to a second surface of said heat flow sensor, which second surface is not in direct contact with said heat conductive material; and, (f) measuring the changes in mass and flow of heat from the sample to the heat sink for the sample disposed on the first face of said piezoelectric substrate.

36. The method of claim 35, wherein said microresonator measures the mass of the sample applied to said first face, and further wherein said heat flow sensor measures the flow of heat from the sample on said first face to the heat sink.

37. The method of claim 35, wherein said heat flow sensor comprises a thermopile.

38. The method of claim 35, wherein said piezoelectric substrate operates in a thickness shear mode.

39. The method of claim 35, wherein said piezoelectric substrate is a heat conductive material.

40. The method of claim 35, wherein said piezoelectric substrate is a quartz crystal.

41. The method of claim 35, wherein said piezoelectric substrate is an AT-cut quartz crystal.

42. The method of claim 35, wherein said heat conductive material further provides a path for the application of radio-frequency power to said piezoelectric substrate.

43. The method of claim 35, wherein said heat conductive material comprises a metallic cylinder with a surface in contact to the first surface of said heat flow sensor.

44. The method of claim 35, wherein said heat conductive material is brass.

45. A method for measuring the mass of a sample and the flow of heat from the sample to a heat sink, the method comprising the steps of:

(a) providing a quartz crystal microbalance capable of measuring the mass of the sample in contact with said quartz crystal microbalance;

(b) providing a heat flow sensor coupled thermally to said quartz crystal microbalance and capable of measuring flow of heat from the sample to a heat sink;

(c) providing a heat sink coupled thermally to said heat flow sensor; and, (d) measuring the changes in mass of the sample and the flow of heat from the sample to the heat sink for the sample disposed on said quartz crystal microbalance.

46. The method of claim 45, wherein said quartz crystal microbalance comprises a quartz substrate having a perimeter, a first face for directly contracting the sample, and a second opposite face isolated from contacting the sample, said quartz substrate having a resonant frequency and capable of producing a measurement signal based on said resonant frequency.

47. The method of claim 46, wherein said method further comprises providing electrodes deposited on the first and second opposite faces of said quartz substrate, said electrodes being capable of supplying electrical signals to and from said quartz substrate.

48. The method of claim 47, wherein said method further comprises providing a heat conductive material extending in a continuous fashion from the perimeter of said quartz substrate to a first surface of said heat flow sensor, wherein said heat conductive material is not in contact with an acoustically active region of said second opposite face.

49. The method of claim 48, wherein said heat flow sensor comprises a thermopile.

50. The method of claim 48, wherein said heat sink material is in contact to a second surface of said heat flow sensor, which second surface is not in direct contact with said heat conductive material.

51. The method of claim 48, wherein said quartz substrate is an AT-cut quartz crystal.

52. The method of claim 48, wherein said heat conductive material further provides a path for the application of radio-frequency power to said quartz substrate.

53. The method of claim 48, wherein said heat conductive material comprises a metallic cylinder with a surface in contact to the first surface of said heat flow sensor.

54. The method of claim 48, wherein said heat conductive material is brass.

55. A measurement sensor comprising:

(a) a microresonator comprising a piezoelectric substrate having a perimeter, a first face for directly contacting a sample, and a second opposite face isolated from contacting the sample, said piezoelectric substrate having a resonant frequency and capable of producing a measurement signal based on said resonant frequency;

(b) a heat flow sensor coupled thermally to said piezoelectric substrate of said microresonator; and (a) a heat sink coupled thermally to said heat flow sensor;

wherein said microresonator is capable of measuring at least one property of the sample in contact with said first face, and said heat flow sensor is capable of measuring the flow of heat from the sample in contact with said first face to said heat sink coupled thermally to said heat flow sensor.

56. The measurement sensor of claim 55, wherein said heat flow sensor is capable of simultaneously measuring the flow of heat from the sample to said heat sink coupled thermally to said heat flow sensor, in real time with the measurement of said at least one property of the sample by said microresonator.

57. The measurement sensor of claim 55, wherein one of said at least one property of the sample measured by said microresonator is selected from the group of properties consisting of:

mass, liquid density, liquid viscosity, polymer modulus, and electrical conductivity.

58. The measurement sensor of claim 55, wherein one of said at least one property of the sample measured by said microresonator is mass.

59. The measurement sensor of claim 55, wherein said microresonator is selected from the group of microresonators consisting of:

bulk acoustic wave sensors, quartz crystal microbalances, surface acoustic wave sensors, flexural plate wave sensors, and acoustic plate mode sensors.

60. A measurement sensor comprising:
(a) a quartz crystal microbalance capable of measuring at least one property of a sample in contact with said quartz crystal microbalance; and
(b) a heat flow sensor coupled thermally to said quartz crystal microbalance and capable of measuring the flow of heat from the sample in contact with said quartz crystal microbalance to a heat sink;
wherein said heat sink is coupled thermally to said heat flow sensor.

61. The measurement sensor of claim 60, wherein said heat flow sensor is capable of simultaneously measuring the flow of heat from the sample to said heat sink coupled thermally to said heat flow sensor, in real time with the measurement of said at least one property of the sample by said quartz crystal microbalance.

62. The measurement sensor of claim 60, wherein one of said at least one property of the sample measured by said quartz crystal microbalance is selected from the group of properties consisting of:

mass, liquid density, liquid viscosity, polymer modulus, and electrical conductivity.

63. The measurement sensor of claim 60, wherein one of said at least one property of the sample measured by said quartz crystal microbalance is mass.

64. A measurement sensor comprising:
(a) an acoustic wave microsensor comprising a piezoelectric substrate having a perimeter, a first face for directly contacting a sample, and a second opposite face isolated from contacting the sample, said piezoelectric substrate having a resonant frequency and capable of producing a measurement signal based on said resonant frequency;
(b) a heat flow sensor coupled thermally to said piezoelectric substrate of said acoustic wave microsensor; and
(c) a heat sink coupled thermally to said heat flow sensor;
wherein said acoustic wave microsensor is capable of measuring at least one property of the sample in contact with said first face, and said heat flow sensor is capable of measuring the flow of heat from the sample in contact with said first face to said heat sink coupled thermally to said heat flow sensor; and wherein said acoustic wave microsensor is selected from the group of acoustic wave microsensors consisting of bulk acoustic wave sensors, surface acoustic wave sensors, flexural plate wave sensors, and acoustic plate mode sensors.

65. The measurement sensor of claim 64, wherein said heat flow sensor is capable of simultaneously measuring the flow of heat from the sample to said heat sink coupled thermally to said heat flow sensor, in real time with the measurement of said at least one property of the sample by said acoustic wave microsensor.

66. The measurement sensor of claim 64, wherein one of said at least one property of the sample measured by said acoustic wave microsensor is selected from the group of properties consisting of:

mass, liquid density, liquid viscosity, polymer modulus, and electrical conductivity.

67. The measurement sensor of claim 64, wherein one of said at least one property of the sample measured by said acoustic wave microsensor is mass.

* * * * *